(12) United States Patent
Petermann et al.

(10) Patent No.: US 7,735,198 B2
(45) Date of Patent: Jun. 15, 2010

(54) PIVOTABLE BRACKET

(75) Inventors: Lothar Petermann, Bad Schwartau (DE); Gunnar Wiegandt, Herrnburg (DE); Stefan Papendieck, Sereetz (DE)

(73) Assignee: Dräger Medical AG & Co. KG, Lübeck (DE)

( * ) Notice: Subject to any disclaimer, the term of this patent is extended or adjusted under 35 U.S.C. 154(b) by 0 days.

(21) Appl. No.: 11/739,856

(22) Filed: Apr. 25, 2007

(65) Prior Publication Data

US 2008/0047101 A1 Feb. 28, 2008

(30) Foreign Application Priority Data

Jul. 14, 2006 (DE) .................. 10 2006 032 749

(51) Int. Cl.
*E05C 17/64* (2006.01)

(52) U.S. Cl. .......................... 16/342; 16/340

(58) Field of Classification Search ............ 16/342, 16/337–340, 240, 241; 248/923, 291.1, 291.12; 248/291.13; 403/91, 101
See application file for complete search history.

(56) References Cited

U.S. PATENT DOCUMENTS

| 4,018,104 A * | 4/1977 | Bland et al. ............... 74/531 |
| 5,101,533 A | 4/1992 | Stenger et al. |
| 5,913,351 A * | 6/1999 | Miura .......................... 16/340 |
| 6,038,739 A * | 3/2000 | Katoh .......................... 16/342 |
| 6,421,878 B1 * | 7/2002 | Kaneko et al. ................ 16/330 |
| 6,539,582 B1 * | 4/2003 | Chae ........................... 16/340 |
| 6,988,294 B2 * | 1/2006 | Birtley ......................... 16/342 |
| 7,143,476 B2 * | 12/2006 | Minami ...................... 16/340 |
| 2005/0066475 A1 | 3/2005 | Minami |

FOREIGN PATENT DOCUMENTS

| DE | 84 04 298.2 | 5/1984 |
| DE | 276 333 A1 | 2/1990 |
| DE | 202005009009 U1 | 8/2005 |
| GB | 1 280 479 | 7/1972 |
| GB | 2 236 800 | 4/1991 |
| JP | 2004-116540 | 4/2004 |
| JP | 2005-321044 | 11/2005 |

* cited by examiner

*Primary Examiner*—William L. Miller
(74) *Attorney, Agent, or Firm*—McGlew and Tuttle, P.C.

(57) ABSTRACT

A pivotable bracket is provided such that a constant moment of friction is present at the hinge (4). A first hinge part (5) is provided, which has a cylindrical pin (6) and a contact surface (11). A second hinge part (12) is provided, which has a bearing bush (13), which can be pushed over the pin (6), with two friction surfaces (15, 16) directed at right angles to the central axis (14). The second hinge part (12) is braced against the contact surface (11) by means of a tensioning device (7, 19, 20, 21, 22) arranged on the upper side of the pin (6).

13 Claims, 3 Drawing Sheets

PIVOTABLE BRACKET

CROSS REFERENCE TO RELATED APPLICATIONS

This application claims the benefit of priority under 35 U.S.C. §119 of German Patent Application DE 10 2006 032 749.7 filed Jul. 14, 2006, the entire contents of which are incorporated herein by reference.

FIELD OF THE INVENTION

The present invention pertains to a pivotable bracket with a hinge and two hinge parts that can be rotated in relation to one another.

BACKGROUND OF THE INVENTION

A bracket of the type mentioned is known from DD 276 333 A1. The tubular support structure has a friction hinge, whose hinge half shells are held together by a screw. By means of the screw, the hinge can either be fixed, so that it cannot be adjusted, or the screw is loosened, so that the object connected to the support structure can be brought into a new position. The frictional force to be overcome for the adjustment of the hinge depends on the prestress of the screw and can be changed in coarse increments only. The user requires that an approximately constant moment of friction be transmitted by means of the hinge.

SUMMARY OF THE INVENTION

The basic object of the present invention is to perfect a bracket of the type mentioned such that a constant moment of friction can be set.

According to the invention, a pivotable bracket is provided comprising a first hinge part including a cylindrical pin having a contact surface and a second hinge part. The first hinge part and the second hinge part form a hinge in which the first hinge part and the second hinge part can be rotated in relation to one another. The second hinge part has a bearing bush pushed over the pin, the bearing bush having two friction surfaces directed at right angles to a bearing bush central axis. A tensioning device or tensioning means is fixed to the pin, wherein one of the friction surfaces is located at the contact surface and another of the friction surfaces is loaded via the tensioning device.

The advantage of the device according to the present invention can be seen in that a hinge part designed as a bearing bush is fastened to a stationary pin in such a way that the frictional force to be overcome for the adjustment is generated predominantly via friction surfaces directed at right angles to the central axis. On its underside, the pin has for this purpose a contact surface, with which the bearing bush is in contact. The other friction surface lying on the upper side of the hinge part is braced with the upper side of the pin via a spring-loaded thrust washer. The contact pressure in the area of the friction surfaces and hence the torque to be overcome for the adjustment can be set by means of the prestressing force of the tensioning means in the form of a thrust washer such that a reproducible, constant moment of friction will be obtained.

It is especially advantageous to provide a layered arrangement comprising two different thrust washers with friction disks located between them. A first embodiment of the thrust washer is connected to the bearing bush in such a way that they are secured against rotation, and the second embodiment of the thrust washer is arranged at the pin via teeth. Friction disks, with which the moment of friction between the hinge parts is generated, are located between the thrust washers. The layered arrangement of the thrust washers is closed on the upper side with the second embodiment of the thrust washer, which is connected to the pin in such a way that they are secured against rotation. Complete uncoupling of the components rotating in relation to one another during pivoting and the stationary components is thus achieved, so that the preset frictional force is preserved over a long use time.

It is especially advantageous to arrange on the upper side of the pin an adjusting element, which can be screwed into the pin, in the form of a handwheel, with which the pressing force on the thrust washers can be increased via a thrust collar acting on the thrust washers. It is possible with the handwheel to individually adapt the moment of friction of the hinge parts without a tool being necessary.

An exemplary embodiment of the present invention is shown in the figure and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
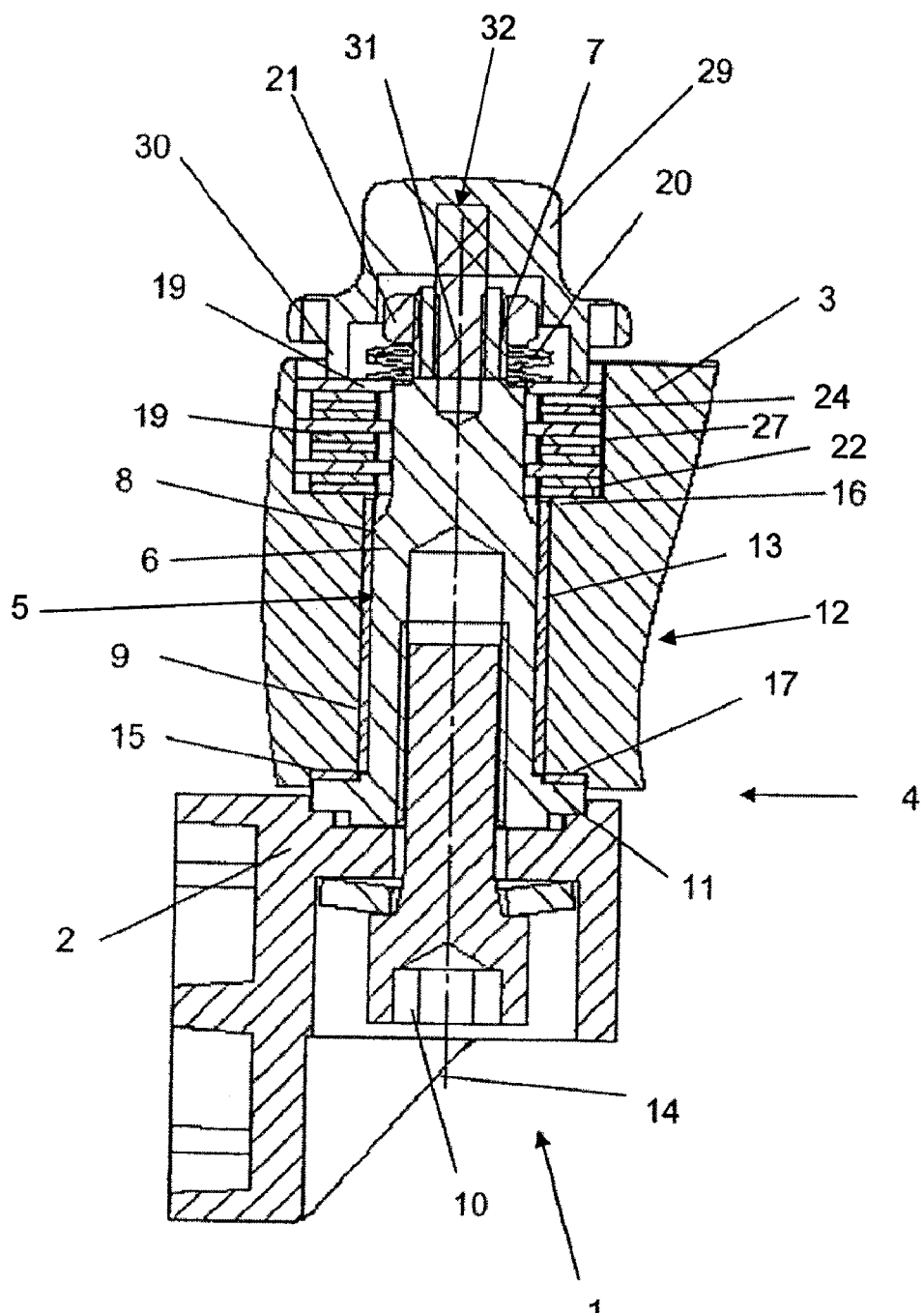
FIG. 1 is a longitudinal sectional view of a pivotable bracket according to the invention.

Referring to the drawings in particular, FIG. 1 schematically shows the longitudinal section of a pivotable bracket 1. The bracket 1 comprises a first bracket section 2, a second bracket section 3 and a hinge 4 between the bracket sections 2, 3. The hinge 4 comprises a first hinge part 5 at the first bracket section 2, which hinge part has a vertically upwardly pointing pin 6 with a threaded bolt 7 and cylindrical bushes 8, 9 that are in contact with the pin 6. The pin 6 is arranged on the first bracket section 2 by means of a fastening screw 10 in such a way that it is secured against rotation and has a disk-shaped contact surface 11 projecting from the pin 6 on its underside.

The second hinge part 12 comprises a bearing bush 13 in the second bracket section 3 and two friction surfaces 15, 16 extending at right angles to the central axis 14. The internal diameter of the bearing bush 13 corresponds to the external diameter of the bushes 8, 9. Corresponding to the view in FIG. 1, a friction disk 17 is located between the lower friction surface 15 and the contact surface 11 of the pin 6.

A first thrust washer 22, which is received in a housing section 27 of the second bracket section 3 in such a way that it is secured against rotation, is received on the upper friction surface 16. This is followed alternatingly by a friction disk 24 and a second thrust washer 19, which is arranged at the pin 6 in such a way that it is secured against rotation in relation to the first thrust washer 22. This is followed by the friction disk 24 and again by the first thrust washer 22. The layered structure comprising thrust washers 19, 22 and friction disks 24 is closed on the upper side by the second thrust washer 19.

The thrust washers 19, 22 and the friction disks 24 are braced against the upper friction surface 16 by means of two plate springs 20, which lie on the topmost, second thrust washer 19, as well as a lock nut 21 at the threaded bolt 7 of the pin 6. Since the thrust washers 19, 22 are either connected to the pin 6 in such a way that they are secured against rotation or to the housing section 27, and the second thrust washer 19 lying on the upper side of the layered structure is connected to the pin in such a way that it is secured against rotation, the second thrust washer 19 has no relative motion relative to the lock nut 21 during the pivoting of the bracket sections 2, 3, so that loosening of the lock nut 21 and hence a reduction of the moment of friction cannot occur.

A handwheel 29 with a thrust collar 30, which is turned into an internal thread 32 on the upper side of the pin 6 by means of a threaded stem 31, is provided for the fine adjustment of the moment of friction within the hinge 4. Depending on the depth to which the threaded stem 31 is screwed in, a varying pressing force is applied by the thrust collar 30 on the thrust washers 19, 22 and the friction disks 24 and the moment of friction is thus changed.

Figure 2:
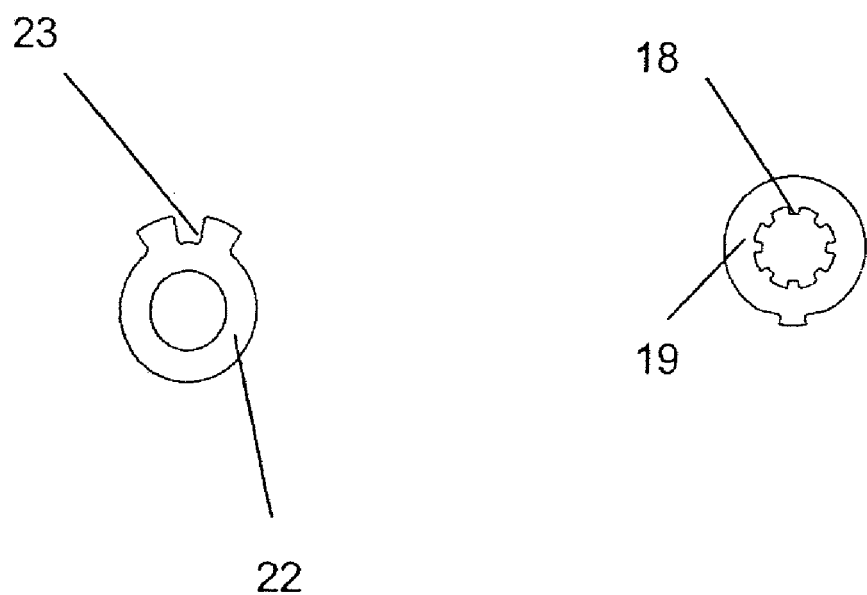
FIG. 2 is a top view of two thrust washers of the pivotable bracket according to the embodiment of FIG. 1.

FIG. 2 shows a top view of the first thrust washer 22 and the second thrust washer 19. The first thrust washer is provided with an outer notch 23 as a means securing against rotation. The second thrust washer has internal teeth 18.

Figure 3:
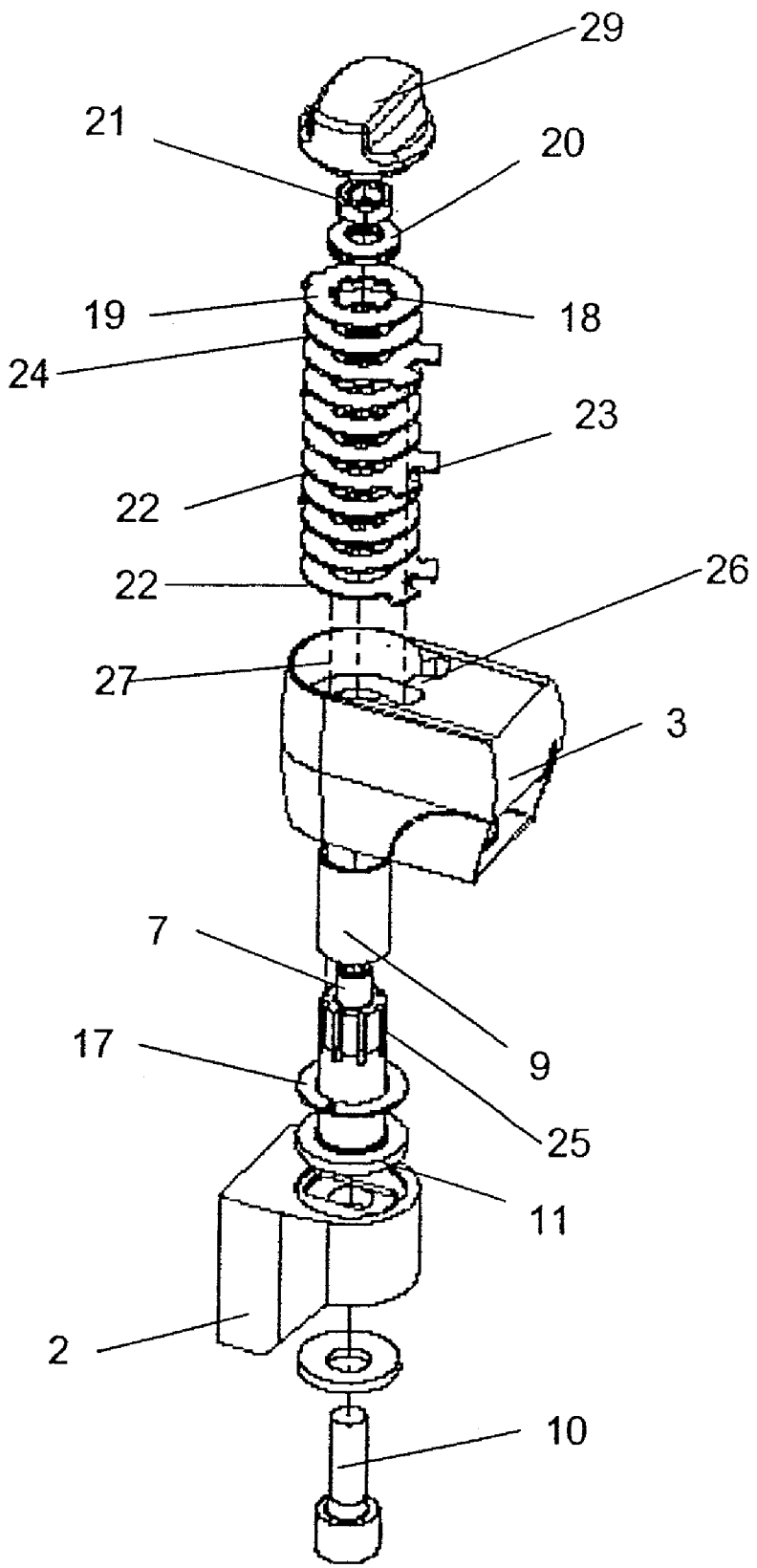
FIG. 3 is a perspective view of the bracket according to FIG. 1.

FIG. 3 illustrates the bracket 1 according to FIG. 1 is a perspective view in the form of an exploded view. Identical components are designated by the same reference numbers as in FIGS. 1 and 2.

The pin 6 has a means securing against rotation in the form of teeth 25, which are arranged distributed over the circumference and mesh with the internal teeth 18 of the second thrust washer 19. A wedge 26, which meshes with the outer notch 23 of the first thrust washer 19, is provided, corresponding to this, within the housing section 27.

While a specific embodiment of the invention has been shown and described in detail to illustrate the application of the principles of the invention, it will be understood that the invention may be embodied otherwise without departing from such principles.

What is claimed is:

1. A pivotable bracket comprising:
   a first hinge part including a cylindrical pin having a contact surface;
   a second hinge part, said first hinge part and said second hinge part forming a hinge in which said first hinge part and said second hinge part can be rotated in relation to one another, said second hinge part having a bearing bush pushed over said pin, said bearing bush having two friction surfaces directed at right angles to a bearing bush central axis;
   a tensioning device fixed to said pin, wherein one of said friction surfaces is located at said contact surface and another of said friction surfaces is loaded via said tensioning device, said tensioning device comprising a threaded bolt at the end of said pin, a locknut, a tensioning spring and thrust washers, said lock nut being connected to said threaded bolt, said tensioning spring being located between said lock nut and one of said thrust washers, wherein said thrust washers comprise a first thrust washer connected to said second hinge part such that said first thrust washer does not rotate relative to said second hinge part and said thrust washers comprise a second thrust washer connected to said pin such that said second thrust washer does not rotate relative to said pin; and
   friction disks wherein said thrust washers are arranged layer by layer with respective ones of said friction disks interposed therebetween.

2. A bracket in accordance with claim 1, further comprising an adjusting element acting on said thrust washers to increase contact pressure, said adjusting element being provided on an upper side of said pin.

3. A bracket in accordance with claim 2, wherein said adjusting element is fastened to said pin by means of a threaded connection which changes the relative position between said adjusting element and said pin.

4. A pivotable bracket comprising:
   a first hinge part including a cylindrical pin having a contact surface;
   a second hinge part, said first hinge part and said second hinge part forming a hinge in which said first hinge part and said second hinge part can be rotated in relation to one another, said second hinge part having a bearing bush pushed over said pin, said bearing bush having two friction surfaces directed at right angles to a bearing bush central axis; and
   a tensioning means comprising elements connected to said first hinge part for rotation therewith and elements connected to said second hinge part for rotation therewith, said tensioning means for loading one of said two friction surfaces located at said contact surface relative to another of said two friction surfaces by applying contact pressure through said elements, wherein said elements connected to said first hinge part comprise a threaded bolt at the end of said pin, a lock nut and a tensioning spring, one or more of said elements connected to said first hinge part and said elements connected to said second hinge part comprising thrust washers, said lock nut being connected to said threaded bolt, said tensioning spring being located between said lock nut and one of said thrust washers.

5. A bracket in accordance with claim 4, wherein said thrust washers comprise a first thrust washer connected to said second hinge part.

6. A bracket in accordance with claim 5, wherein said thrust washers comprise a second thrust washer connected to said pin.

7. A bracket in accordance with claim 6, further comprising friction disks wherein said thrust washers are arranged layer by layer with respective ones of said friction disks interposed therebetween.

8. A bracket in accordance with claim 4, further comprising an adjusting means for acting on said thrust washers to increase contact pressure, said adjusting means being provided on an upper side of said pin.

9. A bracket in accordance with claim 8, wherein said adjusting means is fastened to said pin by means of a threaded connection which changes the relative position between said adjusting means and said pin.

10. A pivotable bracket with a hinge comprising:
    a first hinge part having a cylindrical pin having a contact surface;
    a second hinge part, said first hinge part and said second hinge part being rotatable in relation to one another and relative to a central axis, said second hinge part having a bearing bush pushed over said pin, said bearing bush having two friction surfaces directed at right angles to said central axis;
    a clamping device fixed to said pin;

pressing disks cooperating with said clamping device, one of said friction surfaces being located on a contact surface and the other of said friction surfaces being loaded via said pressing disks and said clamping device, said pressing disks including first pressing disks connected to said second hinge part such that each first pressing disk rotates in unison with said second hinge part and said pressing disks including second pressing disks connected to said pin such that each second pressing disk rotates in unison with said pin; and friction disks, wherein said pressing disks are arranged in a layered pattern via an intermediary of said friction disks.

11. A bracket in accordance with claim 10, wherein said clamping device comprises a threaded bolt at an end of said pin, a lock nut and a tension spring, said lock nut being connected to said threaded bolt, said tension spring being located between said lock nut and one of said pressing disks.

12. A bracket in accordance with claim 10, wherein said clamping device further comprises an adjusting element acting on said pressing disks for increasing a pressing pressure, said adjusting element being provided on an upper side of said pin.

13. A bracket in accordance with claim 12, wherein said adjusting element is fastened to said pin by a threaded connection for changing a relative position between said adjusting element and said pin.

* * * * *